United States Patent [19]

Desmond et al.

[11] Patent Number: 5,840,924
[45] Date of Patent: Nov. 24, 1998

[54] PROCESS OF PREPARING PHENYL HETEROCYCLES USEFUL AS COX-2 INHIBITORS

[75] Inventors: Richard Desmond, Bridgewater; Ulf H. Dolling, Westfield; Lisa F. Frey, Piscataway; Richard D. Tillyer, Westfield; David M. Tschaen, Holmdel, all of N.J.

[73] Assignee: Merck & Co., Inc., Rahway, N.J.

[21] Appl. No.: 876,894

[22] Filed: Jun. 16, 1997

Related U.S. Application Data

[60] Provisional application No. 60/021,200 Jul. 3, 1997.
[51] Int. Cl.⁶ .................................................. C07D 307/58
[52] U.S. Cl. ............................................................ 549/323
[58] Field of Search ............................................. 549/323

[56] References Cited

U.S. PATENT DOCUMENTS

| | | | |
|---|---|---|---|
| 4,585,789 | 4/1986 | Okamoto et al. | 514/461 |
| 4,797,417 | 1/1989 | Okamoto et al. | 514/573 |
| 4,853,473 | 8/1989 | Fischer et al. | 549/326 |
| 4,855,320 | 8/1989 | Chatterjee et al. | 514/473 |
| 4,968,817 | 11/1990 | Brima | 549/295 |
| 5,094,681 | 3/1992 | Kramer et al. | 549/321 |
| 5,207,817 | 5/1993 | Kramer et al. | 504/299 |
| 5,474,995 | 12/1995 | Ducharme et al. | 514/241 |
| 5,550,142 | 8/1996 | Ducharme et al. | 514/365 |

FOREIGN PATENT DOCUMENTS

| | | | |
|---|---|---|---|
| 566175 A2 | 10/1993 | European Pat. Off. | 549/323 |
| WO 91/16055 | 10/1991 | WIPO . | |
| 506175 A2 | 10/1993 | WIPO . | |
| WO 94/15932 | 7/1994 | WIPO . | |
| WO 95/00501 | 1/1995 | WIPO . | |
| WO 95/05376 | 2/1995 | WIPO . | |

OTHER PUBLICATIONS

Joh, et al. Organometallics, vol. 10, pp. 2493–2498 (1991).
Ford et al. Preparation of 2 (5H) Furanones, pp. 173–177 (1967).
ViJay Araghavan, et al. Indian J. Chem. vol. 25B, pp. 760–761 (1986).
Dikshit, et al. Indian J. Chem. vol. 29B, pp. 954–960 (1990).
Doyama, et al. J. Chem. Soch. Chem. Comm. pp. 649–650 (1987).
Ahmed, et al. Rev. Roum. Chim. vol. 38, No. 1, pp. 79–82 (1993).
Ahmed, et al. Egypt. J. Chem. vol. 33, No. 3, pp. 291–295 (1990).
Toda, et al. J. Chem. Soc. Chem. Comm. vol. 18, No. 1, 1234–1235 (1984).
Ohashi, et al. Phytochemistry, vol. 31, pp. 1371–1373 (1992).
Kraph et. al., Chem. Ber. vol. 109, No. 2, pp. 576–596 (1976).
Zaug et. al., J. Heterocycle Chem. vol. 11, No. 5, pp. 797–802 (1974).
Blaguev et. al., Tetrahedron vol. 38, No. 11, pp. 1609–1613 (1982).
Schmit et. al., Tetrahedron vol. 25, No. 44, pp. 5043–5046 (1984).
Ros et. al., J. Org. Chem., vol. 60, No. 17, pp. 5419–5424 (1995).

*Primary Examiner*—Bernard Dentz
*Attorney, Agent, or Firm*—Richard C. Billups; Curtis C. Panzer; David L. Rose

[57] ABSTRACT

The invention encompasses a process for making compounds of Formula I useful in the treatment of inflammation and other cyclooxygenase-2 mediated diseases.

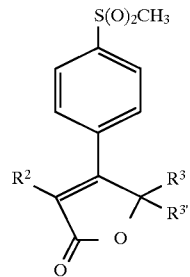

12 Claims, No Drawings

PROCESS OF PREPARING PHENYL HETEROCYCLES USEFUL AS COX-2 INHIBITORS

CROSS REFERENCE TO RELATED APPLICATIONS

This application is a non-provisional application related to U.S. application Ser. No. 60/021,200, filed on Jul. 3, 1997 priority of which is claimed hereunder.

BACKGROUND OF THE INVENTION

This invention concerns a process for making certain anti-inflammatory compounds. In particular, the application concerns a process for making compounds of formula I as disclosed hereinunder, which compounds are potent cyclooxygenase-2 inhibitors.

Non-steroidal, anti inflammatory drugs exert most of their anti inflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar anti inflammatory, antipyretic and analgesic properties to a conventional non-steroidal anti inflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 94/15932 published Jul. 21, 1994 discloses a multi-step method of making bi-aryl furans via bi-aryl lactones, which method utilizes a keto-ester internal cyclization to the lactone. We have found that a significant amount of undesired by-products are produced by use of the disclosed process scheme, due to the external cyclization reactions which compete with the desired internal cyclization. While these byproducts can be removed by suitable separation and purification techniques, we have sought to identify alternative processes to obviate the difficulties. Use of compounds of Formula I as cyclooxygenase-2 inhibitors and methods of making them are disclosed in U.S. Pat. No. 5,474,995, which is hereby incorporated by reference.

SUMMARY OF THE INVENTION

The invention encompasses a process for making compounds of Formula I useful in the treatment of inflammation and other cyclooxygenase-2 mediated diseases.

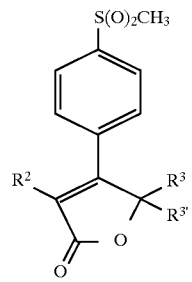

DETAILED DESCRIPTION OF THE INVENTION

In a first aspect, the invention encompasses a process for making compounds of Formula I useful in the treatment of inflammation and other cyclooxygenase-2 mediated diseases

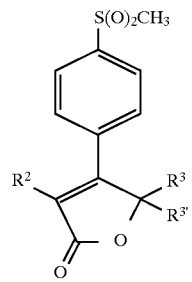

$R^2$ is organic group such as mono- or di substituted phenyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$, and
(7) $C_{1-6}$alkyl,
$R^3$ and $R^{3'}$ are each independently selected from hydrogen and $C_{1-4}$alkyl, comprising:
(b1) reacting in an inert solvent in the presence of an acyl chloride of the formula:
ti $R^{3'}R^3CHC(O)Cl$ and Aluminum chloride, thioanisole

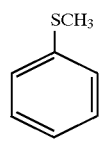

to yield a compound of Formula 3

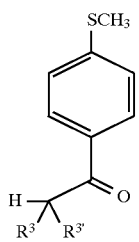
3

For purposes of this specification, the inert solvent shall be defined to include ortho di-chlorobenzene, methylene chloride and chloroform. Ortho di-chlorobenzene is preferred. The molar ratio of Acetyl chloride to thioanisole is typically 0.9:1 to 1.5:1. Preferably excess Acetyl chloride (e.g. 1.2:1) is used. The mole ratio of Aluminum chloride to thioanisole is typically 0.9:1 to 1.5:1. Preferably excess Aluminum chloride (e.g. 1.2:1) is used.

(b2) reacting in an inert solvent in the presence of a phase transfer catalyst, and an oxidizing agent, compound of Formula 3 to yield a compound of Formula 4

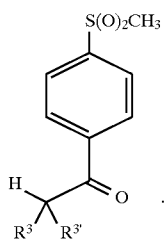
4

For purposes of this specification the phase transfer catalyst is defined to include tricaprylylmethyl ammonium chloride (ALIQUAT) and tetrabutylammonium bromide. For purposes of this specification the oxidizing agent is hydrogen peroxide. The oxidizing agent is optionally accompanied by sodium tungstate or other appropriate catalyst. The molar ratio of Formula 3 to oxidizing agent is typically 0.5:1 to 0.5 to 2. The amount of tungstate is typically 1 to 3 weight % of the amount of Formula 3. The amount of phase transfer catalyst used is typically 1 to 10 weight % of Formula 3.

(b3) reacting in aqueous acetic acid a compound of Formula 4 with Bromine to yield a compound of Formula 2

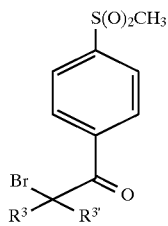
2

The molar ratio of bromine to Formula 4 is typically 0.9:1 to 1.1:1. Hydrogen bromide may be optionally added to initiate the reaction.

(b4) reacting in N,N-dimethylformamide a compound of Formula 2 with an acetic acid derivative of formula

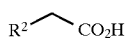

in the presence of an inorganic base to produce a compound of Formula 5a

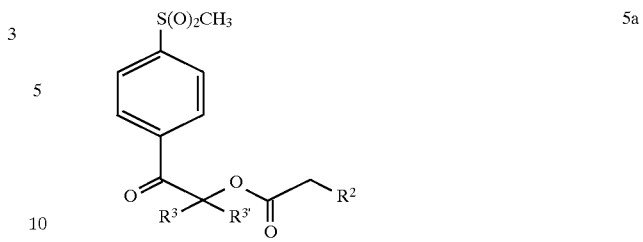
5a

For purposes of this specification, the inorganic base shall include Sodium hydroxide. The molar ratio of the phenyl acetic acid to compound of Formula 2 is typically 0.8:1 to 1:0.8. Preferably, excess phenyl acetic acid is used (e.g. 1.3:1). The molar ratio of inorganic base to Formula 2 is typically about 1:1. Preferably excess inorganic base is used (about 1.1:1).

(b5) treating in a polar aprotic solvent the compound 5a with an organic base to yield a compound of Formula I.

For purposes of this specification, the polar aprotic solvent includes N,N-dimethylformamide, dimethylformamide, dimethylacetamide and N-methylpyrrolidone. The organic base includes diisopropylamine.

The resulting compound of Formula I can then be crystallized from the product of step (b5), preferably at 40° to 60° C.

Scheme 1

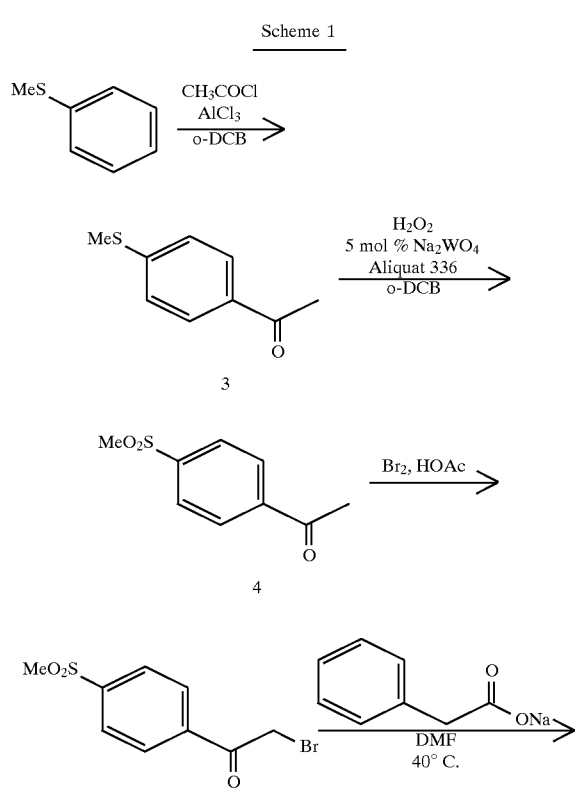

-continued
Scheme 1

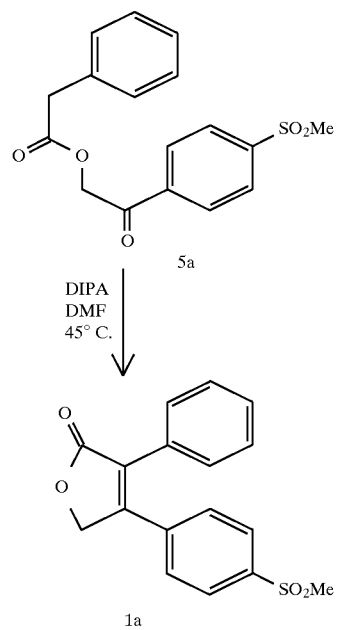

Friedel-Crafts Acylation

The synthesis of bromoketone 2 begins with the Friedel-Crafts reaction between thioanisole and acetyl chloride, to give 4-(methylthio)acetophenone 3 herein referred to as ketosulfide 3).

The Friedel-Crafts acylation of thioanisole (AlCl$_3$-CH$_3$COCl, o-DCB) provided ketosulfide 3 selectively (>100:1 para:ortho). After aqueous workup the layers were separated and the o-DCB solution of ketosulfide 3 (97.5% assay yield) was carried on directly to the next step.

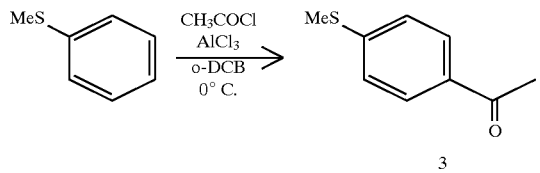

The Friedel-Crafts reaction involves pre-forming the AlCl$_3$-acetyl chloride complex in o-DCB (about 1.2 equiv. of each reagent), followed by addition of thioanisole (1 equiv.). Both of these steps are exothermic and temperature control is desirable.

The use of o-DCB introduces a potential problem, namely solvent acylation by the AlCl$_3$-acetyl chloride complex, to give dichloroacetophenone. The formation of dichloroacetophenone is effectively minimized by conducting the acylation at −5° to 30° C. preferably −5° to 25° C.

The reaction was usually complete within 30 min after the thioanisole addition.

The reaction was quenched by slow transfer into water (exothermic). Applicants have found it desirable to maintain at 25° C. or below.

Sulfide Oxidation

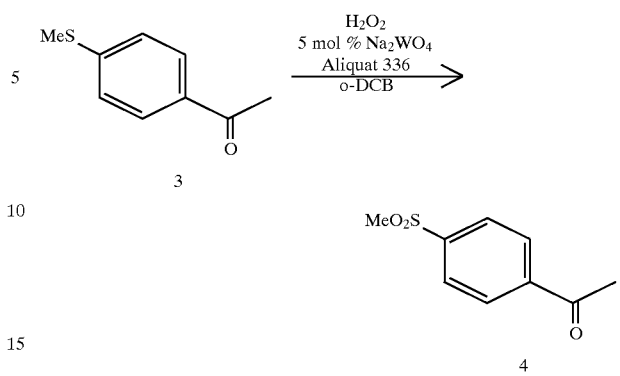

The Friedel-Crafts procedure provided a solution of ketosulfide 3 in o-dichlorobenzene which was to be oxidized directly. The oxidation was carried out by adding aqueous hydrogen peroxide to a mixture consisting of the ketosulfide, o-DCB, water with sodium tungstate, and ALIQUAT 336 as the phase transfer catalyst. Ketosulfone 4 was isolated in 88% yield.

The oxidation was carried out using approximately 1–5 wt % sodium tungstate relative to the ketosulfide. Minimization of the catalyst charge was deemed desirable because preliminary results indicated that tungsten might be trapped in the isolated ketosulfone.

The reaction had an induction period of approximately 15 minutes and it is important to establish that the reaction is underway before charging the full amount of peroxide since initiation of the exothermic reaction at a late stage was potentially hazardous. Oxidation of the sulfide to sulfoxide and the sulfoxide to sulfone were carried out such that both occurred rapidly, thus avoiding a buildup of H$_2$O$_2$ after the first oxidation. This was achieved by addition of H$_2$O$_2$ to the substrate-Na$_2$WO$_4$-ALIQUAT 336 mixture at elevated temperature. Once the oxidation is running, the exotherm maintained the temperature and sometimes cooling was necessary to maintain a reaction temperature of 45°–50° C. Heat was used during the 1–2 hour age to maintain the desired temperature range.

The method of product isolation is based on the solubility of the ketosulfone in o-DCB. As the oxidation neared completion, the ketosulfone precipitates from the reaction mixture. At the end of the reaction, excess H$_2$O$_2$ is destroyed by reaction with aqueous NaHSO$_3$, and the product is isolated by filtration of the three phase mixture. The cake is washed with IPA to remove water and o-DCB and was dried, in vacuo, to give the product in 86–90% yield.

Bromination

The direct bromination of the ketosulfone 4 with bromine in HOAc, initiated with HBr and carried out at ambient temperature, gave a 93% conversion to 2-bromo-4-(methylsulfonyl)acetophenone 2 (herein on referred to as bromoketone 2).

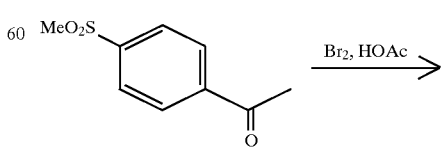

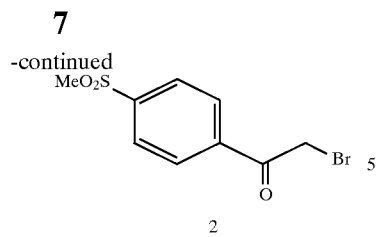

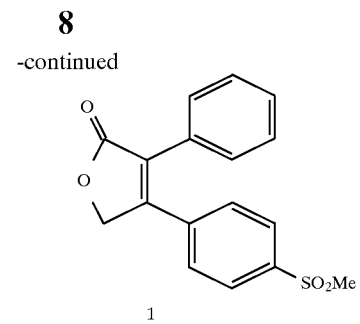

0.96–0.98 equivalents of bromine relative to ketosulfone results in a 93% conversion to bromoketone. Further addition of bromine tends to increase amounts of dibromoketone. The bromination reaction has an induction period ranging from 1–15 minutes on average. The reaction is exothermic and is preferably controlled to 25° to 24° C.

Addition of water (1 vol) to the slurry in HOAc followed by filtration provided an 87% yield of bromoketone 2.

Brominations in acetic acid carried out at preferably 22°–24° C. at concentrations ranging from 3–10 ml acetic acid per gram of ketosulfone.

Coupling-Cyclization

Applicants have surprisingly found that the cyclization reaction was significantly faster in amide solvents (DMF, NMP, DMAC) than in ACN. Clean coupling reactions are achieved using amine bases, inorganic bases and AMBERLITE IRA 900. Inorganic bases are preferred for the coupling since the presence of amine hydrobromide salts (formed during coupling using amine bases) retarded the cyclization reaction. In the cyclization reaction, amine bases are surprisingly superior to inorganic bases such as carbonates and bicarbonates, in terms of product purity. The fastest and cleanest reaction was obtained using diisopropylamine.

The reaction sequence was carried out as follows. Sodium phenylacetate was generated in situ by reaction of phenylacetic acid with NaOH at 40° C. Addition of the bromoketone 2 effected rapid coupling to give 4-(methylsulfonyl) benzoylmethyl phenylacetate 5 (herein referred to as phenylacetic ester 5) which is then cyclized using diisopropylamine (DIA) at 45° C. The product 1 was isolated by direct crystallization from the reaction mixture after addition of aqueous HCl and water.

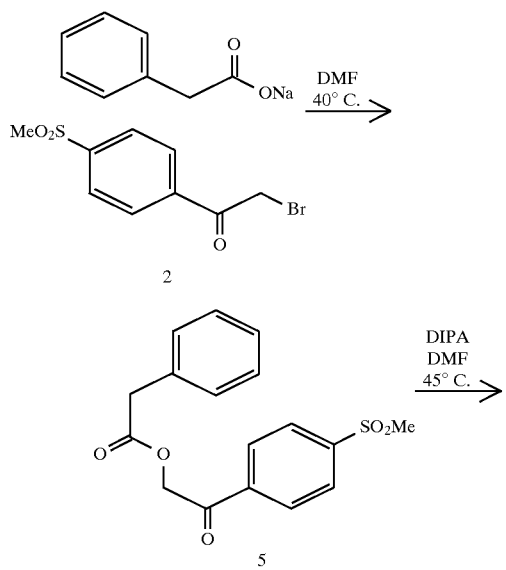

The use of sodium phenylacetate in the coupling reaction with the bromoketone 2 is important due to the high solubility of NaBr (formed during the coupling reaction) in DMF. NaHCO$_3$-phenylacetic acid could be used but the coupling reaction was slow. Potassium phenylacetate (generated in situ from phenylacetic acid and KOH) or KHCO$_3$-phenylacetic acid should not be used as this results in precipitation of KBr, which is trapped in the product during the quench.

The coupling-cyclization sequence is preferably carried out using de-gassed DMF as solvent, since this was found to be advantageous in terms of product color. To avoid color impurities the solvent is degassed such as by nitrogen sparging.

The cyclization reaction is carried out using approximately 3 equiv. of DIA at 45° C. The coupling product (phenylacetic ester 5) is rapidly converted into the aldol intermediates 6 which are then converted into compound 1

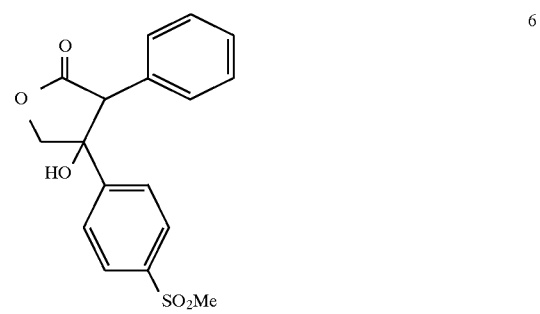

A cyclization reaction run at 40° C. usually required 4.5 hours for complete conversion. Cyclization reactions using approximately 2 equiv of DIA or 2.5 equiv. of DIA at 45° C. required approx. 4.25 h for complete reaction and provided Compound 1 in comparable yield and quality to that obtained using 3 equivalents of base.

The reaction was quenched by the addition of aq. 2N HCl (3.5 equiv. relative to bromoketone) at 20°–30° C. This serves to neutralize the DIA and to effect product crystallization.

Final Product Recrystallization

Acetone and IPA has proven to be an excellent solvent combination for the recrystallization in terms of yield (90–92%), impurity rejection and color rejection. However, the moderate solubility of Compound 1 in acetone (approx. 25 mg/ml at 25° C.) requires a large volume of solvent for batch dissolution and filtration. Subsequent concentration (vacuum distillation) increases processing time, and the need to separate and recycle acetone and IPA by distillation adds to cost and reduces efficiency.

A solution to the productivity issue requires a solvent in which Compound 1 is highly soluble. It has been surprisingly found that DMF-H$_2$O is an excellent solvent combination for the recrystallization in terms of yield (>95%), and impurity and color rejection. In general, however, use of DMF will result in a high level of residual solvent in the crystalized product. We have surprisingly found that when crystallization is carried out at 40° to 60° C., we experience little entrapment of solvent (less than 0.2%). In comparison, when the crystallization is carried out at room temperature, there is significant solvent entrapment (approximately 1 to 2%). Compound 1 has high solubility (135 mg/mL at 25° C.) in DMF, which is well tolerated in the final product. Semi-pure Compound 1 is dissolved in DMF (6.5 mL/g, 50° C.). The solution is filtered, to remove any extraneous matter, and water (8 mL/g) is slowly added (1 h) while maintaining the solution temperature at 50° C. The mixture is cooled to 25° C., aged 30 min and filtered. The cake is washed with DMF-H$_2$O (1:3), H$_2$O, and IPA, and then dried under vacuum (25° C.) to give pure Compound 1 (98% yield).

After the water addition the batch was cooled to 25° C. and aged for 30 min prior to filtration. The batch is filtered and the cake was washed with DMF-H$_2$O (1:2), H$_2$O, and then IPA. The solid was then dried in a vacuum oven at 25° C. to give the final product in 98% yield.

Synthesis of Ketosulphide 3

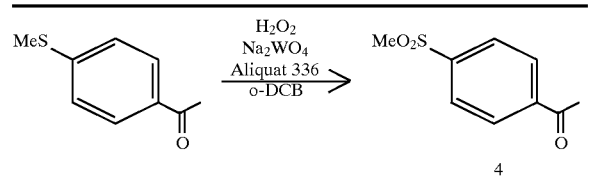

| | MW | mol | equ | amount |
|---|---|---|---|---|
| Thioanisole | 124.21 | 16.10 | 1.0 | 2 kg |
| Acetyl chloride | 78.5 | 19.34 | 1.2 | 1.375 L |
| Aluminum chloride | 133.3 | 19.34 | 1.2 | 2.58 kg |
| o-DCB | | | | 25 L |
| Water | | | | 31 L |

A 50 L 4-neck round bottom flask equipped with a mechanical stirrer, N$_2$ line, and temperature probe was charged with o-DCB. The solution was cooled to −5° C. and AlCl$_3$ was added.

Acetyl chloride was added, neat, via addition funnel, over a period of 10 min. The resulting suspension was cooled to −5° C. and thioanisole was added, via addition funnel, over 40 min. Toward the end of the thioanisole addition a very heavy yellow slurry had formed. Efficient stirring was required (high torque mechanical stirrer). The slurry was aged at −2° C. to +2° C. for 60 min. A 50 L 4-neck round bottom flask equipped with a mechanical stirrer and temperature probe, was charged with H$_2$O (15 L) which was then cooled to 10° C. The reaction mixture (temperature adjusted to +2° C. so that the slurry is mobile enough to be transferred) was transferred slowly into the water (over 1 h), via wide bore teflon cannula, while stirring vigorously. The residual reaction mixture in the vessel was quenched with H$_2$O (2 L), which was then transferred to the quench mixture. During the quench the solution temperature was maintained between 10°–22° C. by controlling the rate of addition and by external cooling (ice-brine cooling bath).

The mixture was stirred vigorously at 10°–25° C. for 1.5 h. The mixture was transferred into a 100 L extraction vessel and the layers were separated. The o-DCB layer (bottom layer) was charged into the extraction vessel, H$_2$O (7 L) was added and the mixture was stirred for 5 min at 25° C. The layers were separated and the o-DCB layer was analyzed by HPLC. A quantitative assay relative to a chromatographed standard indicated the formation of 2.61 kg of ketosulfide 3, a 97.5% assay yield.

The o-DCB solution of product was taken on directly to the next step.

Preparation of Ketosulfone 4

PROCEDURE

| | MW | mol | equ | amount |
|---|---|---|---|---|
| Ketosulfide | 166.23 | 0.59 | 1.0 | 98 g |
| Na$_2$WO$_4$.2H$_2$O | 329.86 | 0.003 | 0.015 | 1.0 g |
| Aliquat 336 | 404.17 | 0.012 | 0.02 | 5.0 g |
| Aqueous 30% H$_2$O$_2$ | 34.02 | 1.47 | 2.5 | 150 mL |
| Aqueous 20% NaHSO$_3$ | | | | 152 mL |
| IPA | | | | 300 mL |
| H$_2$O | | | | 300 mL |
| Sulfuric acid (1M) | | | | 7 mL |

A 1 L 3-neck round bottom flask equipped with a mechanical stirrer, temperature probe, addition funnel, and N$_2$ inlet was charged with sodium tungstate dihydrate (1.0 g as a solution in 20 ml H$_2$O), sulfuric acid (1M, 4 mL), ketosulfide solution (1 L of an o-DCB solution, 98 g, 1 equiv.) and Aliquat 336.

The mixture was heated under a nitrogen atmosphere to 45° C. An addition funnel was charged with 150 ml aqueous 30% hydrogen peroxide and 15 ml was added to the ketosulfide-Na$_2$WO$_4$ mixture. The reaction was aged for 15 minutes and sampled. The remainder of the hydrogen peroxide (135 ml) was added over 1 hour at a temperature of 45° C. The reaction was aged for 30 minutes and assayed.

The mixture was cooled to 18° C. The unreacted peroxide was quenched by the slow addition of aqueous 20 wt % sodium bisulfite solution. The temperature was maintained under 25° C.

The mixture was aged for 30 min at 22° C. and was then filtered. The wet cake was washed once with H$_2$O (100 mL) and once with IPA (300 ml) and was then dried in vacuo at 40° C. (nitrogen sweep) to give 104.7 g of ketosulfone (89.6% yield from thioanisole).

Synthesis of Bromoketone 2

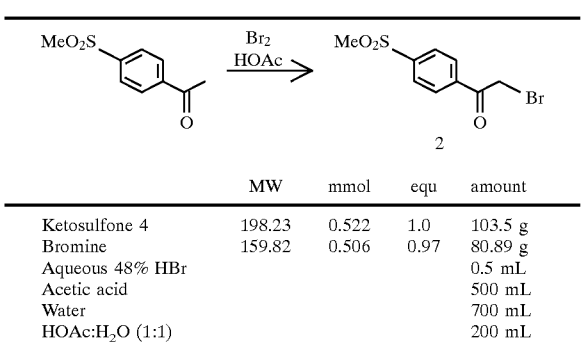

|                    | MW     | mmol  | equ  | amount   |
|--------------------|--------|-------|------|----------|
| Ketosulfone 4      | 198.23 | 0.522 | 1.0  | 103.5 g  |
| Bromine            | 159.82 | 0.506 | 0.97 | 80.89 g  |
| Aqueous 48% HBr    |        |       |      | 0.5 mL   |
| Acetic acid        |        |       |      | 500 mL   |
| Water              |        |       |      | 700 mL   |
| HOAc:H$_2$O (1:1)  |        |       |      | 200 mL   |

A 2 L 3-neck round bottom flask equipped with a mechanical stirrer, temperature probe, addition funnel, and N$_2$ inlet was charged with glacial acetic acid, ketosulfone and aq. 48% HBr.

An addition funnel was charged with bromine. A 10% (8.1 g) charge of bromine gave an orange slurry which was aged 30 min at 25° C. and was then sampled.

The bromination reaction has an induction period of 1–15 min after which bromine was rapidly consumed as it was added. The remainder of the bromine was added over 50 min at 20°–25° C. The resulting pale yellow slurry was aged for 2 h at 22°–25° C.

After ageing the mixture for 2–3 h the batch was filtered. The wet cake was washed once with 200 mL of 1:1 H$_2$O:HOAc and once with H$_2$O (200 mL). The cake was dried in vacuo at 40° C. with a N$_2$ sweep to give 126.0 g of bromoketone (87%).

PREPARATION OF Compound 1

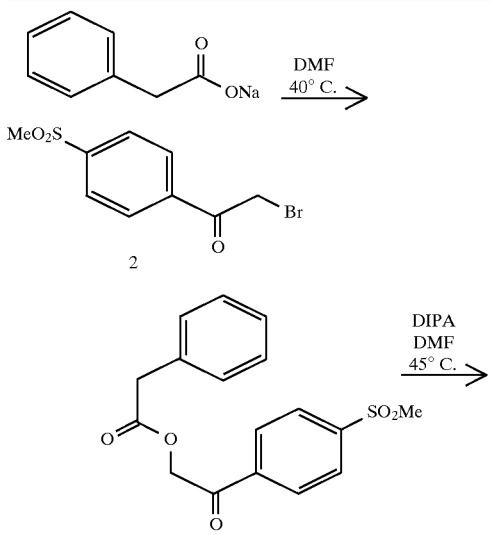

|                       | MW     | mmol | equ  | amount   |
|-----------------------|--------|------|------|----------|
| Bromoketone 2         | 277.13 | 30   | 1.0  | 8.31 g   |
| Phenylacetic acid     | 136.15 | 39   | 1.3  | 5.31 g   |
| NaOH (50 wt%)         |        | 33   | 1.1  | 1.73 mL  |
| Diisopropylamine (DIA)| 101.19 | 90   | 3.0  | 12.6 mL  |
| DMF                   |        |      |      | 152.5 mL |
| 2 N HCl               |        | 105  | 3.5  | 52.5 mL  |
| H$_2$O                |        |      |      | 32 mL    |
| IPA                   |        |      |      | 27.5 mL  |

A 500 mL, baffled, 3-neck round bottom flask equipped with a mechanical stirrer, temperature probe, and nitrogen inlet was charged with phenylacetic acid and DMF (150 mL). The reaction vessel was flushed with N$_2$.

To the solution was added 50 wt % NaOH, resulting in a biphasic mixture. The resulting mixture was stirred vigorously at 4° C. for one hour.

The bromoketone 2 was added to the sodium phenylacetate solution.

The reaction flask was protected from the light due to the known light sensitivity of Compound 1. Diisopropylamine (DIA) was added via syringe (no exotherm), and the batch was aged at 45° C. for 3.5 hours.

The reaction solution was cooled to 20°–25° C., and 2N HCl was added over 1 h via addition funnel, maintaining the temperature between 20° and 30° C.

The product was further precipitated by addition of water (32 mL, via addition funnel) to the reaction slurry over 1 hour.

After ageing 1–2 hours at 25° C., the batch was filtered. The mother liquors were recycled to remove all of the product from the flask. The wet cake was washed once with 10 mL of 1:3 DMF:IPA and once with 20 mL IPA. The cake was dried by suction, to give 7.36 g of semi-pure Compound 1 (78%).

RECRYSTALLIZATION OF Compound 1

|                       | MW  | mol  | equ  | amount   |
|-----------------------|-----|------|------|----------|
| Semi-pure Compound 1  | 314 | 3.18 | 1.0  | 1 kg     |
| DMF                   |     |      |      | 6.67 L   |
| H$_2$O                |     |      |      | 11.83 L  |
| isopropyl alcohol     |     |      |      | 2 L      |

A 12 L 4 neck round bottom flask equipped with a mechanical stirrer, temperature probe and nitrogen inlet was charged with semi-pure Compound 1 and DMF (5.5 L). The mixture was heated to 52° C. over 20 min.

The solution was filtered into a 20 L 4-necked RB flask (equipped with a mechanical stirrer, nitrogen inlet, vacuum inlet and thermocouple) via an in line 1 micron filter. The vessel and line was flushed with 500 mL of DMF. The solution temperature was adjusted to 52° C. and then water (7.5 L) was added via peristaltic pump, over 90 min.

During the water addition, the temperature was maintained between 49° C. and 52° C. Crystals began to form after approximately 10% of the water was added.

The resulting slurry was allowed to cool to 25° C. over 90 min.

The slurry was filtered, the cake was washed with DMF-H$_2$O (1:2, 2 L), H$_2$O (3 L), and then with 2 L IPA. The solid was dried for 12 h under vacuum at 25° C., to give 980 g (98%) of compound 1 as a pale yellow solid.

The following abbreviations have the indicated meanings:

Ac=acetyl
Aliquat=tricaprylylmethyl ammonium chloride
DIA=diisopropylamine (also called DIPA)
DMAC=N,Ndimethylacetamide
DMAP=4-(dimethylamino)pyridine
DMF=N,N-dimethylformamide
HOAc=Acetic acid
IPA=isopropyl alcohol
NMP=1-methyl-2-pyrrolidinone
NSAID=non-steroidal anti-inflammatory drug
oDCB=ortho di-chloro benzene
THF=tetrahydrofuran

What is claimed is:

1. A method of making compounds of Formula I

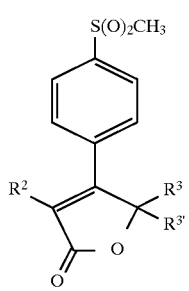

wherein
R$^2$ is mono- or di-substituted phenyl wherein the substituent is selected from the group consisting of
(1) hydrogen,
(2) halo,
(3) C$_{1-6}$alkoxy,
(4) C$_{1-6}$alkylthio,
(5) CN,
(6) CF$_3$, and
(7) C$_{1-6}$alkyl,
R$^3$ and R3' are each independently selected from hydrogen and C$_{1-4}$alkyl,
comprising:
(b4) reacting in N,N-dimethylformamide a compound of Formula 2

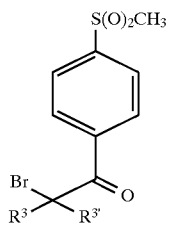

with a phenyl acetic acid of formula

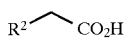

in the presence of an inorganic base to produce a compound of Formula 5a

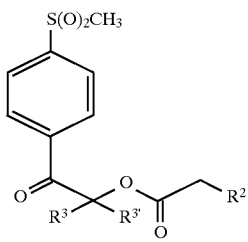

and
(b5) treating in polar aprotic solvent the compound 5a with an organic base to yield a compound of Formula I.

2. A method according to claim 1 wherein the inorganic base is sodium hydroxide.

3. A method according to claim 1 wherein the polar aprotic solvent is N,N-dimethylformamide.

4. A method according to claim 1 wherein step (b5) is followed by crystallization at conducted at approximately 40° to 60° C.

5. A method according to claim 1 wherein
R$^2$ is mono- or di-substituted phenyl wherein the substituent is selected from the group consisting of
(1) hydrogen,
(2) halo,
(3) methoxy,
(4) methyl,
and
R$^3$ and R3' are both hydrogen or are both methyl.

6. A method according to claim 1 wherein
R$^2$ is mono- or di-substituted phenyl wherein the substituent is selected from the group consisting of
(1) hydrogen,
(2) halo,
and
R$^3$ and R3' are both hydrogen or are both methyl.

7. A method according to 1 wherein the compound of Formula I is
(a) 5,5-Dimethyl-3-(3-fluorophenyl)-4-(4-methylsulfonyl)phenyl)-2-(5H)-furanone, or
(b) 3-phenyl-4-(4-(methylsulfonyl)phenyl)-2-(5H)-furanone.

8. A method according to claim 1 comprising
(b3) reacting in aqueous acetic acid a compound of Formula 4

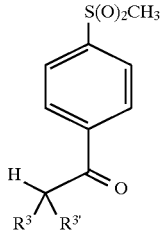

with Bromine to yield a compound of Formula 2

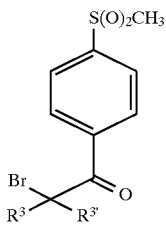

(b4) reacting in N,N-dimethylformamide a compound of Formula 2 with a phenyl acetic acid of formula

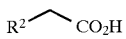

in the presence of an inorganic base to produce a compound of Formula 5a

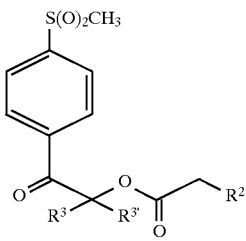

and (b5) treating in a polar aprotic solvent compound 5a with an organic base to yield a compound of Formula I.

9. A method according to claim 8 comprising (b2) reacting in an inert solvent in the presence of a phase transfer catalyst and an oxidizing agent, a compound of Formula 3:

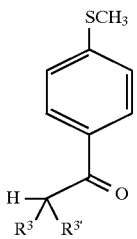

to yield a compound of Formula 4:

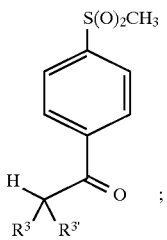

(b3) reacting in aqueous acetic acid a compound of Formula 4 with Bromine to yield a compound of Formula 2:

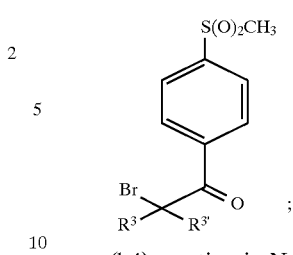

(b4) reacting in N,N-dimethylformamide a compound of Formula 2 with a compound of the formula:

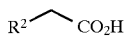

in the presence of an inorganic base to produce a compound of Formula 5a:

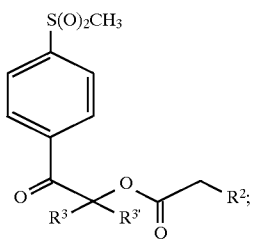

and (b5) treating compound 5a in a polar aprotic solvent with an organic base to yield a compound of Formula I.

10. A method according to claim 9 wherein the phase transfer catalyst of step (b2) is tricaprylylmethyl ammonium chloride, sodium tungstate is added in step (b2) to catalyze the oxidation and hydrogen bromide is added in step (b3) to initiate the reaction.

11. A method according to claim 9 wherein the inert solvent is ortho di-chlorobenzene, the phase transfer catalyst is tricaprylylmethyl ammonium chloride, and the oxidizing agent is hydrogen peroxide.

12. A process according to claim 9 of making a compound of Formula I

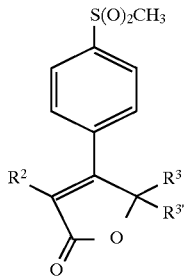

wherein
$R^2$ is a mono- or di substituted phenyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$, and
(7) $C_{1-6}$alkyl,
$R^3$ and R3' are each independently selected from hydrogen and $C_{1-4}$alkyl,
comprising:

(b1) reacting in an inert solvent in the presence of an acyl chloride of the formula: $R^{3'}R^3CHC(O)Cl$ and Aluminum chloride, thioanisole

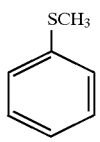

to yield a compound of Formula 3

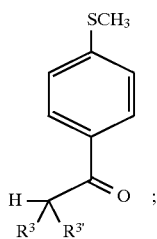

(b2) reacting in an inert solvent in the presence of a phase transfer catalyst, and an oxidizing agent, a compound of Formula 3 to yield a compound of Formula 4

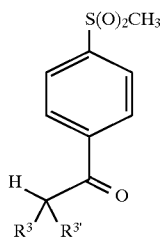

(b3) reacting in aqueous acetic acid a compound of Formula 4 with Bromine to yield a compound of Formula 2

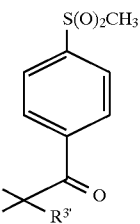

(b4) reacting in N,N-dimethylformamide a compound of Formula 2 with an acetic acid derivative of formula

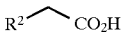

in the presence of an inorganic base to produce a compound of Formula 5a

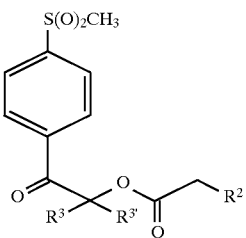

and (b5) treating in a polar aprotic solvent the compound 5a with an organic base to yield a compound of Formula I.

* * * * *